(12) United States Patent
Lesso

(10) Patent No.: US 11,748,462 B2
(45) Date of Patent: Sep. 5, 2023

(54) BIOMETRIC AUTHENTICATION

(71) Applicant: Cirrus Logic International Semiconductor Ltd., Edinburgh (GB)

(72) Inventor: John Paul Lesso, Edinburgh (GB)

(73) Assignee: Cirrus Logic Inc., Austin, TX (US)

( * ) Notice: Subject to any disclaimer, the term of this patent is extended or adjusted under 35 U.S.C. 154(b) by 316 days.

(21) Appl. No.: 17/113,917

(22) Filed: Dec. 7, 2020

(65) Prior Publication Data

US 2021/0117530 A1 Apr. 22, 2021

Related U.S. Application Data

(63) Continuation of application No. 16/118,950, filed on Aug. 31, 2018, now Pat. No. 10,915,614.

(51) Int. Cl.
*G06F 21/00* (2013.01)
*G06F 21/32* (2013.01)
*G10L 15/18* (2013.01)
*G10L 15/22* (2006.01)
*G10L 15/30* (2013.01)

(52) U.S. Cl.
CPC .......... *G06F 21/32* (2013.01); *G10L 15/1815* (2013.01); *G10L 15/22* (2013.01); *G10L 15/30* (2013.01)

(58) Field of Classification Search
CPC ......... G06F 21/32; G10L 15/22; G10L 15/30; G10L 15/1815
See application file for complete search history.

(56) References Cited

U.S. PATENT DOCUMENTS

| 5,197,113 A | 3/1993 | Mumolo |
| 5,568,559 A | 10/1996 | Makino |
| 5,710,866 A | 1/1998 | Alleva et al. |
| 5,787,187 A | 7/1998 | Bouchard et al. |
| 5,838,515 A | 11/1998 | Mortazavi et al. |
| 6,182,037 B1 | 1/2001 | Maes |

(Continued)

FOREIGN PATENT DOCUMENTS

| AU | 2015202397 B2 | 5/2015 |
| CN | 1497970 A | 5/2004 |

(Continued)

OTHER PUBLICATIONS

International Search Report and Written Opinion of the International Searching Authority, International Application No. PCT/GB2019/052302, dated Oct. 2, 2019.

(Continued)

*Primary Examiner* — Jeffrey C Pwu
*Assistant Examiner* — William A Corum, Jr.
(74) *Attorney, Agent, or Firm* — Jackson Walker L.L.P

(57) ABSTRACT

A method for authenticating a user of an electronic device is disclosed. The method comprises: responsive to detection of a trigger event indicative of a user interaction with the electronic device, generating an audio probe signal to play through an audio transducer of the electronic device; receiving a first audio signal comprising a response of the user's ear to the audio probe signal; receiving a second audio signal comprising speech of the user; and applying an ear biometric algorithm to the first audio signal and a voice biometric algorithm to the second audio signal to authenticate the user as an authorised user.

20 Claims, 5 Drawing Sheets

(56) References Cited

U.S. PATENT DOCUMENTS

| | | |
|---|---|---|
| 6,229,880 B1 | 5/2001 | Reformato et al. |
| 6,249,237 B1 | 6/2001 | Prater |
| 6,343,269 B1 | 1/2002 | Harada et al. |
| 6,480,825 B1 | 11/2002 | Sharma et al. |
| 7,016,833 B2 | 3/2006 | Gable et al. |
| 7,039,951 B1 | 5/2006 | Chaudhari et al. |
| 7,418,392 B1 | 8/2008 | Mozer et al. |
| 7,492,913 B2 | 2/2009 | Connor et al. |
| 8,442,824 B2 | 5/2013 | Aley-Raz et al. |
| 8,489,399 B2 | 7/2013 | Gross |
| 8,577,046 B2 | 11/2013 | Aoyagi |
| 8,856,541 B1 | 10/2014 | Chaudhury et al. |
| 8,997,191 B1 | 3/2015 | Stark et al. |
| 9,049,983 B1 | 6/2015 | Baldwin |
| 9,171,548 B2 | 10/2015 | Valius et al. |
| 9,305,155 B1 | 4/2016 | Vo et al. |
| 9,317,736 B1 | 4/2016 | Siddiqui |
| 9,390,726 B1 | 7/2016 | Smus et al. |
| 9,430,629 B1 | 8/2016 | Ziraknejad et al. |
| 9,484,036 B2 | 11/2016 | Kons et al. |
| 9,548,979 B1 | 1/2017 | Johnson et al. |
| 9,600,064 B2 | 3/2017 | Lee et al. |
| 9,613,640 B1 | 4/2017 | Balamurali et al. |
| 9,641,585 B2 | 5/2017 | Kvaal et al. |
| 9,646,261 B2 | 5/2017 | Agrafioli et al. |
| 9,659,562 B2 | 5/2017 | Lovitt |
| 9,665,784 B2 | 5/2017 | Derakhshani et al. |
| 9,706,304 B1 | 7/2017 | Kelso et al. |
| 9,865,253 B1 | 1/2018 | De Leon et al. |
| 9,984,314 B2 | 5/2018 | Philipose et al. |
| 9,990,926 B1 | 6/2018 | Pearce |
| 10,032,451 B1 | 7/2018 | Mamkina et al. |
| 10,063,542 B1 | 8/2018 | Kao |
| 10,079,024 B1 | 9/2018 | Bhimanaik et al. |
| 10,097,914 B2 | 10/2018 | Petrank |
| 10,192,553 B1 | 1/2019 | Chenier et al. |
| 10,204,625 B2 | 2/2019 | Mishra et al. |
| 10,210,685 B2 | 2/2019 | Borgmeyer |
| 10,255,922 B1 | 4/2019 | Sharifi et al. |
| 10,277,581 B2 | 4/2019 | Chandrasekharan et al. |
| 10,305,895 B2 | 5/2019 | Barry et al. |
| 10,318,580 B2 | 6/2019 | Topchy et al. |
| 10,334,350 B2 | 6/2019 | Petrank |
| 10,339,290 B2 | 7/2019 | Valendi et al. |
| 10,460,095 B2 | 10/2019 | Boesen |
| 10,467,509 B2 | 11/2019 | Albadawi et al. |
| 10,692,492 B2 | 6/2020 | Rozen et al. |
| 10,733,987 B1 | 8/2020 | Govender et al. |
| 10,847,165 B2 | 11/2020 | Lesso |
| 10,915,614 B2 | 2/2021 | Lesso |
| 10,977,349 B2 | 4/2021 | Suh et al. |
| 11,017,252 B2 | 5/2021 | Lesso |
| 11,023,755 B2 | 6/2021 | Lesso |
| 11,037,574 B2 | 6/2021 | Lesso |
| 11,051,117 B2 | 6/2021 | Lesso |
| 11,164,588 B2 | 11/2021 | Alonso et al. |
| 11,276,409 B2 | 3/2022 | Lesso |
| 2002/0169608 A1 | 11/2002 | Tamir et al. |
| 2002/0194003 A1 | 12/2002 | Mozer |
| 2003/0033145 A1 | 2/2003 | Petrushin |
| 2003/0177006 A1 | 9/2003 | Ichikawa et al. |
| 2003/0177007 A1 | 9/2003 | Kanazawa et al. |
| 2003/0182119 A1 | 9/2003 | Junqua et al. |
| 2004/0030550 A1 | 2/2004 | Liu |
| 2004/0141418 A1 | 7/2004 | Matsuo et al. |
| 2004/0230432 A1 | 11/2004 | Liu et al. |
| 2005/0060153 A1 | 3/2005 | Gable et al. |
| 2005/0107130 A1 | 5/2005 | Peterson, II |
| 2005/0171774 A1 | 8/2005 | Applebaum et al. |
| 2006/0116874 A1 | 6/2006 | Samuelsson et al. |
| 2006/0171571 A1 | 8/2006 | Chan et al. |
| 2007/0055517 A1 | 3/2007 | Spector |
| 2007/0129941 A1 | 6/2007 | Tavares |
| 2007/0185718 A1 | 8/2007 | Di Mambro et al. |
| 2007/0233483 A1 | 10/2007 | Kuppuswamy et al. |
| 2007/0250920 A1 | 10/2007 | Lindsay |
| 2007/0276658 A1 | 11/2007 | Douglass |
| 2008/0040615 A1 | 2/2008 | Carper et al. |
| 2008/0071532 A1 | 3/2008 | Ramakrishnan et al. |
| 2008/0082510 A1 | 4/2008 | Wang et al. |
| 2008/0223646 A1 | 9/2008 | White |
| 2008/0262382 A1 | 10/2008 | Akkermans et al. |
| 2008/0285813 A1 | 11/2008 | Holm |
| 2009/0087003 A1* | 4/2009 | Zurek ............ G06V 40/10 704/E15.001 |
| 2009/0105548 A1 | 4/2009 | Bart |
| 2009/0167307 A1 | 7/2009 | Kopp |
| 2009/0232361 A1 | 9/2009 | Miller |
| 2009/0281809 A1 | 11/2009 | Reuss |
| 2009/0319270 A1 | 12/2009 | Gross |
| 2010/0004934 A1 | 1/2010 | Hirose et al. |
| 2010/0076770 A1 | 3/2010 | Ramaswamy |
| 2010/0106502 A1 | 4/2010 | Farrell et al. |
| 2010/0106503 A1 | 4/2010 | Farrell et al. |
| 2010/0204991 A1 | 8/2010 | Ramakrishnan et al. |
| 2010/0328033 A1 | 12/2010 | Kamei |
| 2011/0051907 A1* | 3/2011 | Jaiswal ............ G10L 17/22 379/88.04 |
| 2011/0075857 A1 | 3/2011 | Aoyagi |
| 2011/0142268 A1 | 6/2011 | Iwakuni et al. |
| 2011/0246198 A1 | 10/2011 | Asenjo et al. |
| 2011/0276323 A1 | 11/2011 | Seyfetdinov |
| 2011/0314530 A1 | 12/2011 | Donaldson |
| 2011/0317848 A1 | 12/2011 | Ivanov et al. |
| 2012/0110341 A1 | 5/2012 | Beigi |
| 2012/0223130 A1 | 9/2012 | Knopp et al. |
| 2012/0224456 A1 | 9/2012 | Visser et al. |
| 2012/0249328 A1 | 10/2012 | Xiong |
| 2012/0323796 A1 | 12/2012 | Udani |
| 2013/0024191 A1 | 1/2013 | Krutsch et al. |
| 2013/0058488 A1 | 3/2013 | Cheng et al. |
| 2013/0080167 A1 | 3/2013 | Mozer |
| 2013/0132091 A1 | 5/2013 | Skerpac |
| 2013/0225128 A1 | 8/2013 | Gomar |
| 2013/0227678 A1 | 8/2013 | Kang |
| 2013/0247082 A1 | 9/2013 | Wang et al. |
| 2013/0279297 A1 | 10/2013 | Wulff et al. |
| 2013/0279724 A1 | 10/2013 | Stafford et al. |
| 2013/0289999 A1 | 10/2013 | Hymel |
| 2014/0059347 A1 | 2/2014 | Dougherty et al. |
| 2014/0149117 A1 | 5/2014 | Bakish et al. |
| 2014/0172430 A1 | 6/2014 | Rutherford et al. |
| 2014/0188770 A1 | 7/2014 | Agrafioti et al. |
| 2014/0237576 A1 | 8/2014 | Zhang et al. |
| 2014/0241597 A1 | 8/2014 | Leite |
| 2014/0293749 A1 | 10/2014 | Gervaise |
| 2014/0307876 A1 | 10/2014 | Agiomyrgiannakis et al. |
| 2014/0330568 A1 | 11/2014 | Lewis et al. |
| 2014/0337945 A1 | 11/2014 | Jia et al. |
| 2014/0343703 A1 | 11/2014 | Topchy et al. |
| 2014/0358353 A1 | 12/2014 | Ibanez-Guzman et al. |
| 2014/0358535 A1 | 12/2014 | Lee et al. |
| 2015/0006163 A1 | 1/2015 | Liu et al. |
| 2015/0028996 A1 | 1/2015 | Agrafioti et al. |
| 2015/0033305 A1 | 1/2015 | Shear et al. |
| 2015/0036462 A1 | 2/2015 | Calvarese |
| 2015/0088509 A1 | 3/2015 | Gimenez et al. |
| 2015/0089616 A1 | 3/2015 | Brezinski et al. |
| 2015/0112682 A1 | 4/2015 | Rodriguez et al. |
| 2015/0134330 A1 | 5/2015 | Baldwin et al. |
| 2015/0161370 A1 | 6/2015 | North et al. |
| 2015/0161459 A1 | 6/2015 | Boczek |
| 2015/0168996 A1 | 6/2015 | Sharpe et al. |
| 2015/0245154 A1 | 8/2015 | Dadu et al. |
| 2015/0261944 A1 | 9/2015 | Hosom et al. |
| 2015/0276254 A1 | 10/2015 | Nemcek et al. |
| 2015/0301796 A1 | 10/2015 | Visser et al. |
| 2015/0332665 A1 | 11/2015 | Mishra et al. |
| 2015/0347734 A1* | 12/2015 | Beigi ............ H04L 9/3268 726/28 |
| 2015/0356974 A1 | 12/2015 | Tani et al. |
| 2015/0371639 A1 | 12/2015 | Foerster et al. |
| 2016/0007118 A1 | 1/2016 | Lee et al. |
| 2016/0026781 A1 | 1/2016 | Boczek |

(56) References Cited

U.S. PATENT DOCUMENTS

| | | |
|---|---|---|
| 2016/0066113 A1 | 3/2016 | Elkhatib et al. |
| 2016/0071516 A1 | 3/2016 | Lee et al. |
| 2016/0086607 A1 | 3/2016 | Aley-Raz et al. |
| 2016/0086609 A1 | 3/2016 | Yue et al. |
| 2016/0111112 A1 | 4/2016 | Hayakawa |
| 2016/0125877 A1 | 5/2016 | Foerster et al. |
| 2016/0125879 A1 | 5/2016 | Lovitt |
| 2016/0147987 A1 | 5/2016 | Jang et al. |
| 2016/0148012 A1 | 5/2016 | Khitrov et al. |
| 2016/0182998 A1 | 6/2016 | Galal et al. |
| 2016/0210407 A1 | 7/2016 | Hwang et al. |
| 2016/0217321 A1 | 7/2016 | Gottleib |
| 2016/0217795 A1 | 7/2016 | Lee et al. |
| 2016/0234204 A1 | 8/2016 | Rishi et al. |
| 2016/0248768 A1 | 8/2016 | McLaren et al. |
| 2016/0314790 A1 | 10/2016 | Tsujikawa et al. |
| 2016/0324478 A1 | 11/2016 | Goldstein |
| 2016/0330198 A1 | 11/2016 | Stern et al. |
| 2016/0371555 A1 | 12/2016 | Derakhshani |
| 2016/0372139 A1 | 12/2016 | Cho et al. |
| 2017/0011406 A1 | 1/2017 | Tunnell et al. |
| 2017/0049335 A1 | 2/2017 | Duddy |
| 2017/0068805 A1 | 3/2017 | Chandrasekharan et al. |
| 2017/0078780 A1 | 3/2017 | Qian et al. |
| 2017/0110117 A1 | 4/2017 | Chakladar et al. |
| 2017/0110121 A1 | 4/2017 | Warford et al. |
| 2017/0112671 A1 | 4/2017 | Goldstein |
| 2017/0116995 A1 | 4/2017 | Ady et al. |
| 2017/0134377 A1 | 5/2017 | Tokunaga et al. |
| 2017/0150254 A1 | 5/2017 | Bakish et al. |
| 2017/0161482 A1 | 6/2017 | Eltoft et al. |
| 2017/0162198 A1 | 6/2017 | Chakladar et al. |
| 2017/0169828 A1 | 6/2017 | Sachdev |
| 2017/0200451 A1 | 7/2017 | Bocklet et al. |
| 2017/0213268 A1 | 7/2017 | Puehse et al. |
| 2017/0214687 A1 | 7/2017 | Klein et al. |
| 2017/0231534 A1 | 8/2017 | Agassy et al. |
| 2017/0242990 A1 | 8/2017 | Chien |
| 2017/0256270 A1 | 9/2017 | Singaraju et al. |
| 2017/0279815 A1 | 9/2017 | Chung et al. |
| 2017/0287490 A1 | 10/2017 | Biswal et al. |
| 2017/0293749 A1 | 10/2017 | Baek et al. |
| 2017/0323644 A1 | 11/2017 | Kawato |
| 2017/0347180 A1 | 11/2017 | Petrank |
| 2017/0347348 A1 | 11/2017 | Masaki et al. |
| 2017/0351487 A1 | 12/2017 | Aviles-Casco Vaquero et al. |
| 2017/0373655 A1 | 12/2017 | Mengad et al. |
| 2018/0018974 A1 | 1/2018 | Zass |
| 2018/0032712 A1 | 2/2018 | Oh et al. |
| 2018/0039769 A1 | 2/2018 | Saunders et al. |
| 2018/0047393 A1 | 2/2018 | Tian et al. |
| 2018/0060552 A1 | 3/2018 | Pellom et al. |
| 2018/0060557 A1 | 3/2018 | Valenti et al. |
| 2018/0096120 A1 | 4/2018 | Boesen |
| 2018/0107866 A1 | 4/2018 | Li et al. |
| 2018/0108225 A1 | 4/2018 | Mappus et al. |
| 2018/0113673 A1 | 4/2018 | Sheynblat |
| 2018/0121161 A1 | 5/2018 | Ueno et al. |
| 2018/0146370 A1 | 5/2018 | Krishnaswamy et al. |
| 2018/0166071 A1 | 6/2018 | Lee et al. |
| 2018/0174600 A1 | 6/2018 | Chaudhuri et al. |
| 2018/0176215 A1 | 6/2018 | Perotti et al. |
| 2018/0187969 A1 | 7/2018 | Kim et al. |
| 2018/0191501 A1 | 7/2018 | Lindemann |
| 2018/0197525 A1 | 7/2018 | Kikuhara et al. |
| 2018/0232201 A1 | 8/2018 | Holtmann |
| 2018/0232511 A1 | 8/2018 | Bakish |
| 2018/0233142 A1 | 8/2018 | Koishida et al. |
| 2018/0239955 A1 | 8/2018 | Rodriguez et al. |
| 2018/0240463 A1 | 8/2018 | Perotti |
| 2018/0254046 A1 | 9/2018 | Khoury et al. |
| 2018/0289354 A1 | 10/2018 | Cvijanovic et al. |
| 2018/0292523 A1 | 10/2018 | Orenstein et al. |
| 2018/0308487 A1 | 10/2018 | Goel et al. |
| 2018/0324518 A1* | 11/2018 | Dusan ............ H04R 1/1091 |
| 2018/0330727 A1 | 11/2018 | Tulli |
| 2018/0336716 A1 | 11/2018 | Ramprashad et al. |
| 2018/0336901 A1 | 11/2018 | Masaki et al. |
| 2018/0342237 A1 | 11/2018 | Lee et al. |
| 2018/0349585 A1 | 12/2018 | Ahn et al. |
| 2018/0352332 A1 | 12/2018 | Tao |
| 2018/0358020 A1 | 12/2018 | Chen et al. |
| 2018/0366124 A1 | 12/2018 | Cilingir et al. |
| 2018/0374487 A1 | 12/2018 | Lesso |
| 2018/0376234 A1 | 12/2018 | Petrank |
| 2019/0005963 A1 | 1/2019 | Alonso et al. |
| 2019/0005964 A1 | 1/2019 | Alonso et al. |
| 2019/0013033 A1 | 1/2019 | Bhimanaik et al. |
| 2019/0027152 A1 | 1/2019 | Huang et al. |
| 2019/0030452 A1 | 1/2019 | Fassbender et al. |
| 2019/0042871 A1 | 2/2019 | Pogorelik |
| 2019/0043512 A1 | 2/2019 | Huang et al. |
| 2019/0065478 A1 | 2/2019 | Tsujikawa et al. |
| 2019/0098003 A1 | 3/2019 | Ota |
| 2019/0103115 A1 | 4/2019 | Lesso |
| 2019/0114496 A1 | 4/2019 | Lesso |
| 2019/0114497 A1 | 4/2019 | Lesso |
| 2019/0115030 A1 | 4/2019 | Lesso |
| 2019/0115032 A1 | 4/2019 | Lesso |
| 2019/0115033 A1 | 4/2019 | Lesso |
| 2019/0115046 A1 | 4/2019 | Lesso |
| 2019/0122670 A1 | 4/2019 | Roberts et al. |
| 2019/0147888 A1 | 5/2019 | Lesso |
| 2019/0149920 A1 | 5/2019 | Putzeys et al. |
| 2019/0149932 A1 | 5/2019 | Lesso |
| 2019/0180014 A1 | 6/2019 | Kovvali et al. |
| 2019/0197755 A1 | 6/2019 | Vats |
| 2019/0199935 A1 | 6/2019 | Danielsen et al. |
| 2019/0228778 A1 | 7/2019 | Lesso |
| 2019/0228779 A1 | 7/2019 | Lesso |
| 2019/0246075 A1 | 8/2019 | Khadloya et al. |
| 2019/0260731 A1 | 8/2019 | Chandrasekharan et al. |
| 2019/0287536 A1 | 9/2019 | Sharifi et al. |
| 2019/0294629 A1 | 9/2019 | Wexler et al. |
| 2019/0295554 A1 | 9/2019 | Lesso |
| 2019/0304470 A1 | 10/2019 | Ghaeemaghami et al. |
| 2019/0306594 A1 | 10/2019 | Aumer et al. |
| 2019/0306613 A1 | 10/2019 | Qian et al. |
| 2019/0311722 A1 | 10/2019 | Caldwell |
| 2019/0313014 A1 | 10/2019 | Welbourne et al. |
| 2019/0318035 A1 | 10/2019 | Blanco et al. |
| 2019/0356588 A1 | 11/2019 | Shahraray et al. |
| 2019/0371330 A1 | 12/2019 | Lin et al. |
| 2019/0372969 A1 | 12/2019 | Chang et al. |
| 2019/0373438 A1 | 12/2019 | Amir et al. |
| 2019/0392145 A1 | 12/2019 | Komogortsev |
| 2019/0394195 A1 | 12/2019 | Chari et al. |
| 2020/0035247 A1 | 1/2020 | Boyadjiev et al. |
| 2020/0184057 A1 | 6/2020 | Mukund |
| 2020/0204937 A1 | 6/2020 | Lesso |
| 2020/0227071 A1 | 7/2020 | Lesso |
| 2020/0265834 A1 | 8/2020 | Lesso et al. |
| 2020/0286492 A1 | 9/2020 | Lesso |
| 2021/0303669 A1 | 9/2021 | Lesso |
| 2022/0382846 A1 | 12/2022 | Koshinaka et al. |

FOREIGN PATENT DOCUMENTS

| | | |
|---|---|---|
| CN | 1937955 A | 3/2007 |
| CN | 101228787 A | 7/2008 |
| CN | 101578637 A | 11/2009 |
| CN | 102246228 A | 11/2011 |
| CN | 103109495 A | 5/2013 |
| CN | 103477604 A | 12/2013 |
| CN | 104038625 A | 9/2014 |
| CN | 104252860 A | 12/2014 |
| CN | 104956715 A | 9/2015 |
| CN | 105185380 A | 12/2015 |
| CN | 105244031 A | 1/2016 |
| CN | 105702263 A | 6/2016 |
| CN | 105869630 A | 8/2016 |
| CN | 105913855 A | 8/2016 |
| CN | 105933272 A | 9/2016 |
| CN | 105938716 A | 9/2016 |

(56) References Cited

FOREIGN PATENT DOCUMENTS

| | | |
|---|---|---|
| CN | 106297772 A | 1/2017 |
| CN | 106531172 A | 3/2017 |
| CN | 106537889 A | 3/2017 |
| CN | 107251573 A | 10/2017 |
| EP | 1205884 A2 | 5/2002 |
| EP | 1600791 A1 | 11/2005 |
| EP | 1701587 A1 | 9/2006 |
| EP | 1928213 A1 | 6/2008 |
| EP | 1965331 A2 | 9/2008 |
| EP | 2660813 A1 | 11/2013 |
| EP | 2704052 A2 | 3/2014 |
| EP | 2860706 A2 | 4/2015 |
| EP | 3016314 A1 | 5/2016 |
| EP | 3156978 A1 | 4/2017 |
| EP | 3466106 A1 | 4/2019 |
| GB | 2375205 A | 11/2002 |
| GB | 2493849 A | 2/2013 |
| GB | 2499781 A | 9/2013 |
| GB | 2515527 A | 12/2014 |
| GB | 2541466 A | 2/2017 |
| GB | 2551209 A | 12/2017 |
| JP | 2003058190 A | 2/2003 |
| JP | 2006010809 A | 1/2006 |
| JP | 2010086328 A | 4/2010 |
| TW | 200820218 A | 5/2008 |
| WO | 9834216 A2 | 8/1998 |
| WO | 0208147 A1 | 10/2002 |
| WO | 02/103680 A2 | 12/2002 |
| WO | 2006054205 A1 | 5/2006 |
| WO | 2007034371 A2 | 3/2007 |
| WO | 2008113024 A1 | 9/2008 |
| WO | 2010066269 A1 | 6/2010 |
| WO | 2013022930 A1 | 2/2013 |
| WO | 2013154790 A1 | 10/2013 |
| WO | 2014040124 A1 | 3/2014 |
| WO | 2015117674 A1 | 8/2015 |
| WO | 2015163774 A1 | 10/2015 |
| WO | 2016003299 A1 | 1/2016 |
| WO | 2017055551 A | 4/2017 |
| WO | 2017203484 A1 | 11/2017 |
| WO | 2019002831 A1 | 1/2019 |
| WO | 2019008387 A1 | 1/2019 |
| WO | 2019008389 A1 | 1/2019 |
| WO | 2019008392 A1 | 1/2019 |

OTHER PUBLICATIONS

Liu, Yuan et al., "Speaker verification with deep features", Jul. 2014, in International Joint Conference on Neural networks (IJCNN), pp. 747-753, IEEE.
International Search Report and Written Opinion of the International Searching Authority, International Application No. PCT/GB2018/051927, dated Sep. 25, 2018.
Combined Search and Examination Report under Sections 17 and 18(3), UKIPO, Application No. 1801530.5, dated Jul. 25, 2018.
International Search Report and Written Opinion of the International Searching Authority, International Application No. PCT/GB2018/051924, dated Sep. 26, 2018.
Combined Search and Examination Report under Sections 17 and 18(3), UKIPO, Application No. 1801526.3, dated Jul. 25, 2018.
International Search Report and Written Opinion of the International Searching Authority, International Application No. PCT/GB2018/051931, dated Sep. 27, 2018.
Combined Search and Examination Report under Sections 17 and 18(3), UKIPO, Application No. 1801527.1, dated Jul. 25, 2018.
International Search Report and Written Opinion of the International Searching Authority, International Application No. PCT/GB2018/051925, dated Sep. 26, 2018.
Combined Search and Examination Report under Sections 17 and 18(3), UKIPO, Application No. 1801528.9, dated Jul. 25, 2018.
International Search Report and Written Opinion of the International Searching Authority, International Application No. PCT/GB2018/051928, dated Dec. 3, 2018.
Combined Search and Examination Report under Sections 17 and 18(3), UKIPO, Application No. 1801532.1, dated Jul. 25, 2018.
Lim, Zhi Hao et al., An Investigation of Spectral Feature Partitioning for Replay Attacks Detection, Proceedings of APSIPA Annual Summit and Conference 2017, Dec. 12-15, 2017, Malaysia, pp. 1570-1573.
International Search Report and Written Opinion of the International Searching Authority, International Application No. PCT/GB2018/053274, dated Jan. 24, 2019.
Beigi, Homayoon, "Fundamentals of Speaker Recognition," Chapters 8-10, ISBN: 978-0-378-77592-0; 2011.
Li, Lantian et al., "A Study on Replay Attack and Anti-Spoofing for Automatic Speaker Verification", Interspeech 2017, Jan. 1, 2017, pp. 92-96.
Li, Zhi et al., "Compensation of Hysteresis Nonlinearity in Magnetostrictive Actuators with Inverse Multiplicative Structure for Preisach Model", IEE Transactions on Automation Science and Engineering, vol. 11, No. 2, Apr. 1, 2014, pp. 613-619.
Partial International Search Report of the International Searching Authority, International Application No. PCT/GB2018/052905, dated Jan. 25, 2019.
Further Search Report under Sections 17 (6), UKIPO, Application No. GB1719731.0, dated Nov. 26, 2018.
Combined Search and Examination Report, UKIPO, Application No. GB1713695.3, dated Feb. 19, 2018.
Zhang et al., An Investigation of Deep-Learing Frameworks for Speaker Verification Antispoofing—IEEE Journal of Selected Topics in Signal Processes, Jun. 1, 2017.
Combined Search and Examination Report under Sections 17 and 18(3), UKIPO, Application No. GB1804843.9, dated Sep. 27, 2018.
Wu et al., Anti-Spoofing for text-Independent Speaker Verification: an Initial Database, Comparison of Countermeasures, and Human Performance, IEEE/ACM Transactions on Audio, Speech, and Language Processing, Issue Date: Apr. 2016.
Combined Search and Examination Report under Sections 17 and 18(3), UKIPO, Application No. GB1803570.9, dated Aug. 21, 2018.
Combined Search and Examination Report under Sections 17 and 18(3), UKIPO, Application No. GB1801661.8, dated Jul. 30, 2018.
Combined Search and Examination Report under Sections 17 and 18(3), UKIPO, Application No. GB1801663.4, dated Jul. 18, 2018.
Combined Search and Examination Report under Sections 17 and 18(3), UKIPO, Application No. GB1801664.2, dated Aug. 1, 2018.
Combined Search and Examination Report under Sections 17 and 18(3), UKIPO, Application No. GB1719731.0, dated May 16, 2018.
Combined Search and Examination Report, UKIPO, Application No. GB1801874.7, dated Jul. 25, 2018.
Combined Search and Examination Report under Sections 17 and 18(3), UKIPO, Application No. GB1801659.2, dated Jul. 26, 2018.
International Search Report and Written Opinion of the International Searching Authority, International Application No. PCT/GB2018/052906, dated Jan. 14, 2019.
International Search Report and Written Opinion of the International Searching Authority, International Application No. PCT/GB2019/050185, dated Apr. 2, 2019.
Combined Search and Examination Report under Sections 17 and 18(3), UKIPO, Application No. GB1809474.8, dated Jul. 23, 2018.
Ajmera, et al., "Robust Speaker Change Detection," IEEE Signal Processing Letters, vol. 11, No. 8, pp. 649-651, Aug. 2004.
International Search Report and Written Opinion of the International Searching Authority, International Application No. PCT/GB2018/051760, dated Aug. 3, 2018.
International Search Report and Written Opinion of the International Searching Authority, International Application No. PCT/GB2018/051787, dated Aug. 16, 2018.
Villalba, Jesus et al., Preventing Replay Attacks on Speaker Verification Systems, International Carnahan Conference on Security Technology (ICCST), 2011 IEEE, Oct. 18, 2011, pp. 1-8.
International Search Report and Written Opinion of the International Searching Authority, International Application No. PCT/GB2018/051765, dated Aug. 16, 2018.
Combined Search and Examination Report under Sections 17 and 18(3), UKIPO, Application No. GB1713697.9, dated Feb. 20, 2018.

(56) References Cited

OTHER PUBLICATIONS

Chen et al., "You Can Hear but You Cannot Steal: Defending Against Voice Impersonation Attacks on Smartphones", Proceedings of the International Conference on Distributed Computing Systems, PD: Jun. 5, 2017.
International Search Report and Written Opinion of the International Searching Authority, International Application No. PCT/GB2018/052907, dated Jan. 15, 2019.
Combined Search and Examination Report under Sections 17 and 18(3), UKIPO, Application No. GB1713699.5, dated Feb. 21, 2018.
International Search Report and Written Opinion of the International Searching Authority, International Application No. PCT/GB2019/052143, dated Sep. 17, 2019.
Lucas, Jim, What Is Electromagnetic Radiation? Live Science, Mar. 13, 2015, NY, NY.
Brownlee, Jason, A Gentle Introduction to Autocorrelation and Partial Autocorrelation, Feb. 6, 2017, https://machinelearningmastery.com/gentle-introduction-autocorrelation-partial-autocorrelation/, accessed Apr. 28, 2020.
Wu, Libing, et al., LVID: a Multimodal Biometricas Authentication System on Smartphones, IEEE Transactions on Information Forensics and Security, Vo. 15, 2020, pp. 1572-1585.
Wang, Qian, et al., VoicePop: a Pop Noise based Anti-spoofing System for Voice Authentication on Smartphones, IEEE INFOCOM 2019—IEEE Conference on Computer Communications, Apr. 29-May 2, 2019, pp. 2062-2070.
Examination Report under Section 18(3), UKIPO, Application No. GB1918956.2, dated Jul. 29, 2021.
Examination Report under Section 18(3), UKIPO, Application No. GB1918965.3, dated Aug. 2, 2021.
Combined Search and Examination Report under Sections 17 and 18(3), UKIPO, Application No. GB2105613.0, dated Sep. 27, 2021.
Combined Search and Examination Report under Sections 17 and 18(3), UKIPO, Application No. GB2114337.5, dated Nov. 3, 2021.
Ohtsuka, Takahiro and Kasuya, Hideki, Robust ARX Speech Analysis Method Taking Voice Source Pulse Train Into Account, Journal of the Acoustical Society of Japan, 58, 7, pp. 386-397, 2002.
Wikipedia, Voice (phonetics), https://en.wikipedia.org/wiki/Voice_(phonetics), accessed Jun. 1, 2020.
Zhang et al., DolphinAttack: Inaudible Voice Commands, Retrieved from Proceedings of the 2017 ACM SIGSAC Conference on Computer and Communications Security, Aug. 2017.
Song, Liwei, and Prateek Mittal, Poster: Inaudible Voice Commands, Proceedings of the 2017 ACM SIGSAC Conference on Computer and Communications Security, Aug. 2017.
Fortuna, Andrea, [Online], DolphinAttack: inaudiable voice commands allow attackers to control Siri, Alexa and other digital assistants, Sep. 2017.
First Office Action, China National Intellectual Property Administration, Patent Application No. 2018800418983, dated May 29, 2020.
International Search Report and Written Opinion, International Application No. PCT/GB2020/050723, dated Jun. 16, 2020.
Liu, Yuxi et al., "Earprint: Transient Evoked Otoacoustic Emission for Biometrics", IEEE Transactions on Information Forensics and Security, IEEE, Piscataway, NJ, US, vol. 9, No. 12, Dec. 1, 2014, pp. 2291-2301.
Seha, Sherif Nagib Abbas et al., "Human recognition using transient auditory evoked potentials: a preliminary study", IET Biometrics, IEEE, Michael Faraday House, Six Hills Way, Stevenage, HERTS., UK, vol. 7, No. 3, May 1, 2018, pp. 242-250.
Liu, Yuxi et al., "Biometric identification based on Transient Evoked Otoacoustic Emission", IEEE International Symposium on Signal Processing and Information Technology, IEEE, Dec. 12, 2013, pp. 267-271.
Toth, Arthur R., et al., Synthesizing Speech from Doppler Signals, ICASSP 2010, IEEE, pp. 4638-4641.
Boesen, U.S. Appl. No. 62/403,045, filed Sep. 30, 2017.
Meng, Y. et al., "Liveness Detection for Voice User Interface via Wireless Signals in IoT Environment," in IEEE Transactions on Dependable and Secure Computing, doi: 10.1109/TDSC.2020.2973620.
Zhang, L. et al., Hearing Your Voice is Not Enough: an Articulatory Gesture Based Liveness Detection for Voice Authentication, CCS '17: Proceedings of the 2017 ACM SIGSAC Conference on Computer and Communications Security, Oct. 2017 pp. 57-71.
First Office Action, China National Intellectual Property Administration, Application No. 2018800720846, dated Mar. 1, 2021.
Combined Search and Examination Report under Sections 17 and 18(3), UKIPO, Application No. GB2112228.8, dated May 17, 2022.
Search Report under Section 17, UKIPO, Application No. GB2202521.7, dated Jun. 21, 2022.
Combined Search and Examination Report, United Kingdom Intellectual Property Office, Application No. GB2210986.2, dated Nov. 15, 2022.
First Office Action, China National Intellectual Property Administration, Application No. 201800658351, dated Feb. 4, 2023.
Search Report, China National Intellectual Property Administration, Application No. 201800658351, dated Feb. 2, 2023.
First Office Action, China National Intellectual Property Administration, Application No. 2018800452077, dated Feb. 25, 2023.
First Office Action, China National Intellectual Property Administration, Application No. 2018800452787, dated Mar. 14, 2023.
First Office Action, China National Intellectual Property Administration, Patent Application No. 2018800419187, dated Feb. 28, 2023, dated Apr. 28, 2023.
Notice of Preliminary Rejection, Korean Intellectual Property Office, Patent Application No. 10-2020-7002065, dated Apr. 17, 2023.
Notice of Preliminary Rejection, Korean Intellectual Property Office, Patent Application No. 10-2020-7002061, dated Apr. 27, 2023.
Wu et al., A study on replay attack and anti-spoofing for text-dependent speaker verification, Signal and Information Processing Association Annual Summit and Conference (APSIPA), 2014 Asia-Pacific, Dec. 9-12, 2014, IEEE.

* cited by examiner

BIOMETRIC AUTHENTICATION

This application is a continuation of U.S. patent application Ser. No. 16/118,950, filed Aug. 31, 2018, which is incorporated by reference herein in its entirety.

TECHNICAL FIELD

Embodiments of the disclosure relate to biometric authentication, and particularly to methods, apparatus and computer-readable mediums for authenticating a user based on ear biometric data.

BACKGROUND

It is known that the acoustic properties of a user's ear, whether the outer parts (known as the pinna or auricle), the ear canal or both, differ substantially between individuals and can therefore be used as a biometric to identify the user. One or more loudspeakers or similar transducers positioned close to or within the ear generate a stimulus, and one or more microphones similarly positioned close to or within the ear detect the response of the ear to the stimulus. One or more features may be extracted from the response signal, and used to characterize an individual.

For example, the ear canal is a resonant system, and therefore one feature which may be extracted from the response signal is the resonant frequency of the ear canal. If the measured resonant frequency (i.e. in the response signal) differs from a stored resonant frequency for the user, a biometric algorithm coupled to receive and analyse the response signal may return a negative result. Other features of the response signal may be similarly extracted and used to characterize the individual. For example, the features may comprise one or more mel frequency cepstrum coefficients. More generally, the transfer function between the stimulus and the measured response signal (or features of the transfer function) may be determined, and compared to a stored transfer function (or stored features of the transfer function) which is characteristic of the user.

Other acoustic properties of a user's ear include otoacoustic emissions, whether spontaneous (i.e., generated by the ear without external stimulation) or evoked (i.e., generated by the ear in response to a stimulus signal such as one or more pure tones, a tone burst, etc.). Such otoacoustic emissions may also differ between individuals and can therefore be used to discriminate between individuals or to identify a particular individual.

One problem faced by biometric algorithms is the need to achieve acceptable performance in two respects. First, the algorithm should provide acceptable security so that unauthorised users are not falsely recognized as authorised users. The likelihood that the algorithm will accept an access attempt by an unauthorised user is known as the false acceptance rate (FAR), and should be kept low if the algorithm is to provide reasonable security. Second, the algorithm should work reliably, so that authorised users are not falsely rejected as unauthorised. The likelihood that the algorithm will reject an access attempt by an authorised user is known as the false rejection rate (FRR), and should also be kept low if the algorithm is not to prove frustrating for authorised users seeking authentication.

The problem is that these two performance requirements conflict with each other. A low FRR can be achieved by relaxing the requirements for a user to achieve authentication. However, this will also have the consequence of increasing the FAR. Conversely, a low FAR can be achieved by making the requirements for a user to achieve authentication stricter. However, this will have the consequence of increasing the FRR.

One way to decrease both FAR and FRR is to increase the efficacy of the biometric algorithm itself. However, designing the algorithm to achieve high performance is difficult. Further, the efficacy may depend on factors which are outside the designers' control. For example, the efficacy of the algorithm may depend on the quality of the biometric data (e.g., noise levels, etc.), or the discriminatory nature of the biometric itself.

One known technique for improving the efficacy of the authentication is to combine (or "fuse") multiple authentication processes together, whether biometric or not. For example, a user may be required to input a security password or pin number in addition to providing a voice input (e.g., for voice biometric authentication). The authentication processes may be combined using score-level fusion, or result-level fusion. In the former case, separate scores are obtained for each authentication process indicating the likelihood that a user is an authorised user. Those scores are then combined and compared to a threshold to determine whether the user should be authenticated as the authorised user. In the latter case, separate results are obtained for each authentication process (e.g., through separate comparison of each score to a corresponding threshold) and then combined. For example, a user may be authenticated only if the individual authentication results are all positive. By fusing multiple authentication processes in this way, the FAR and FRR values for the combined authentication process can be much lower than the FAR and FRR values associated with an individual authentication process.

However, it can be time consuming and inconvenient to provide multiple inputs as part of an authentication process. Users typically want authentication to be both reliable and secure, while taking as little time as possible. Preferably, the authentication process should even be invisible to the user, such that they are authenticated without even realising that an authentication process has taken place.

SUMMARY

Embodiments of the present disclosure seek to address these and other problems.

For example, in one aspect the present disclosure provides a method for authenticating a user of an electronic device. The method comprises: responsive to detection of a trigger event indicative of a user interaction with the electronic device, generating an audio probe signal to play through an audio transducer of the electronic device; receiving a first audio signal comprising a response of the user's ear to the audio probe signal; receiving a second audio signal comprising speech of the user; and applying an ear biometric algorithm to the first audio signal and a voice biometric algorithm to the second audio signal to authenticate the user as an authorised user.

In one embodiment, the trigger event comprises a predetermined keyword spoken by the user. In such an embodiment, the method may further comprise additionally applying the voice biometric algorithm to the predetermined keyword (which may also be comprised within the second audio signal) to authenticate the user as an authorised user.

Another aspect of the disclosure provides an authentication device for authenticating a user of an electronic device. The authentication device comprises: an audio signal generation module for generating, responsive to detection of a trigger event indicative of a user interaction with the electronic device, an audio probe signal to play through an audio transducer of the electronic device; one or more inputs for receiving a first audio signal comprising a response of the user's ear to the audio probe signal, and a second audio signal comprising speech of the user; and a biometric authentication module for utilizing an ear biometric algorithm on the first audio signal and a voice biometric algorithm on the second audio signal to authenticate the user as an authorised user.

In one embodiment, the trigger event comprises a predetermined keyword spoken by the user. In such an embodiment, the biometric authentication module is further for utilizing the voice biometric algorithm on the predetermined keyword to authenticate the user as an authorised user.

A further aspect of the disclosure provides an electronic device comprising an authentication device as set out above. The electronic device may be portable and/or battery powered, such as a smartphone, an audio player, a mobile or cellular phone, or a handset.

BRIEF DESCRIPTION OF THE DRAWINGS

For a better understanding of examples of the present disclosure, and to show more clearly how the examples may be carried into effect, reference will now be made, by way of example only, to the following drawings in which.

DETAILED DESCRIPTION

As noted above, ear biometric data may be acquired by the generation of an acoustic stimulus (which may be audible or non-audible, e.g., ultrasonic), and the detection of an acoustic response of the ear to the acoustic stimulus. One or more features may be extracted from the response signal, and used to characterize the individual. The acoustic response of the ear may relate to the acoustic transfer function of the ear, and/or otoacoustic emissions from the ear. Alternatively or additionally, otoacoustic emissions may be spontaneous, and detected without any requirement for an acoustic stimulus.

Ear biometric data may be acquired using a personal audio device. As used herein, the term "personal audio device" is any electronic device which is suitable for, or configurable to, provide audio playback substantially to only a single user. Some examples of suitable personal audio devices are shown in FIGS. 1a and 1b.

Figure 1A:
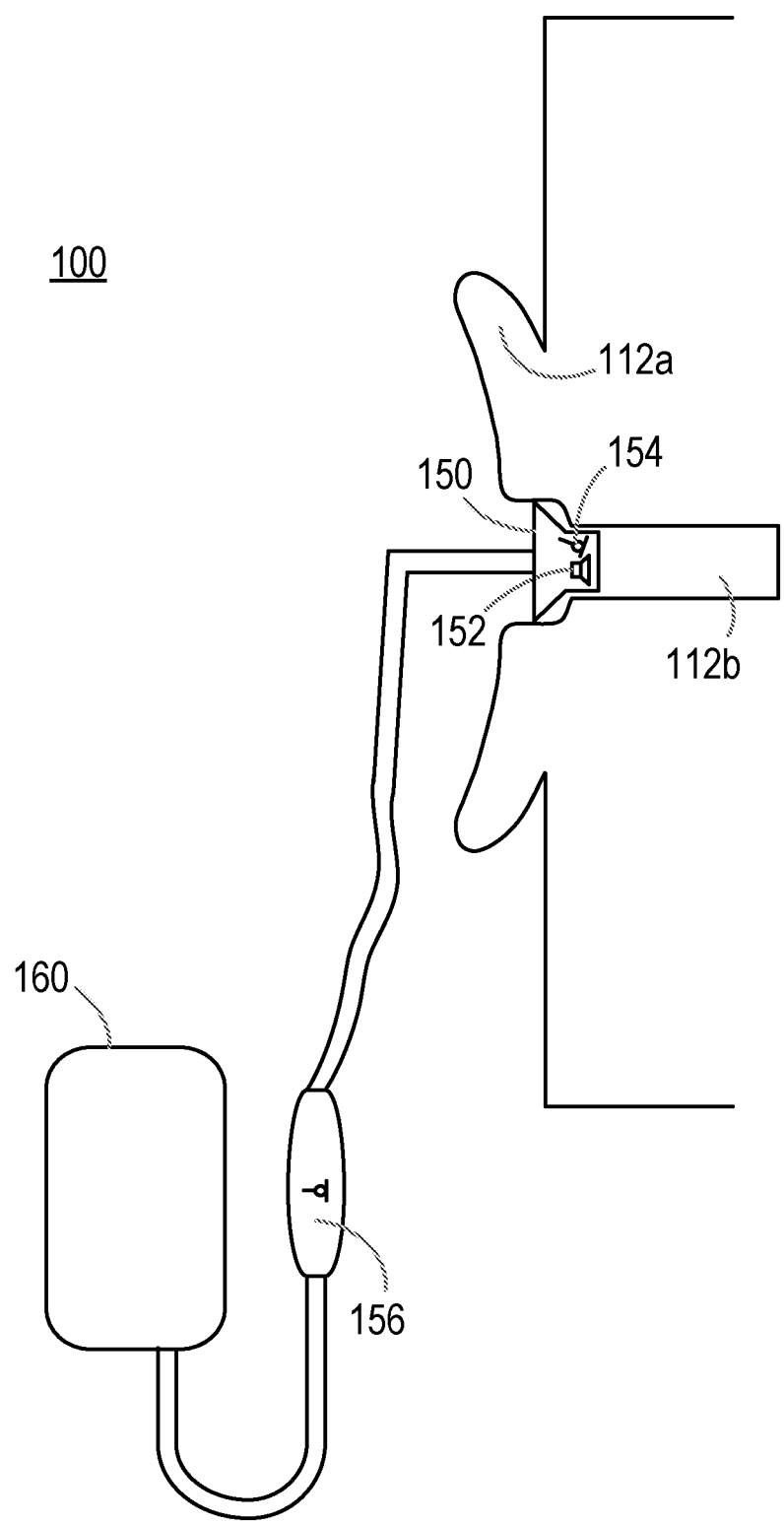
FIG. 1a shows a personal audio device according to one configuration.
Figure 1B:
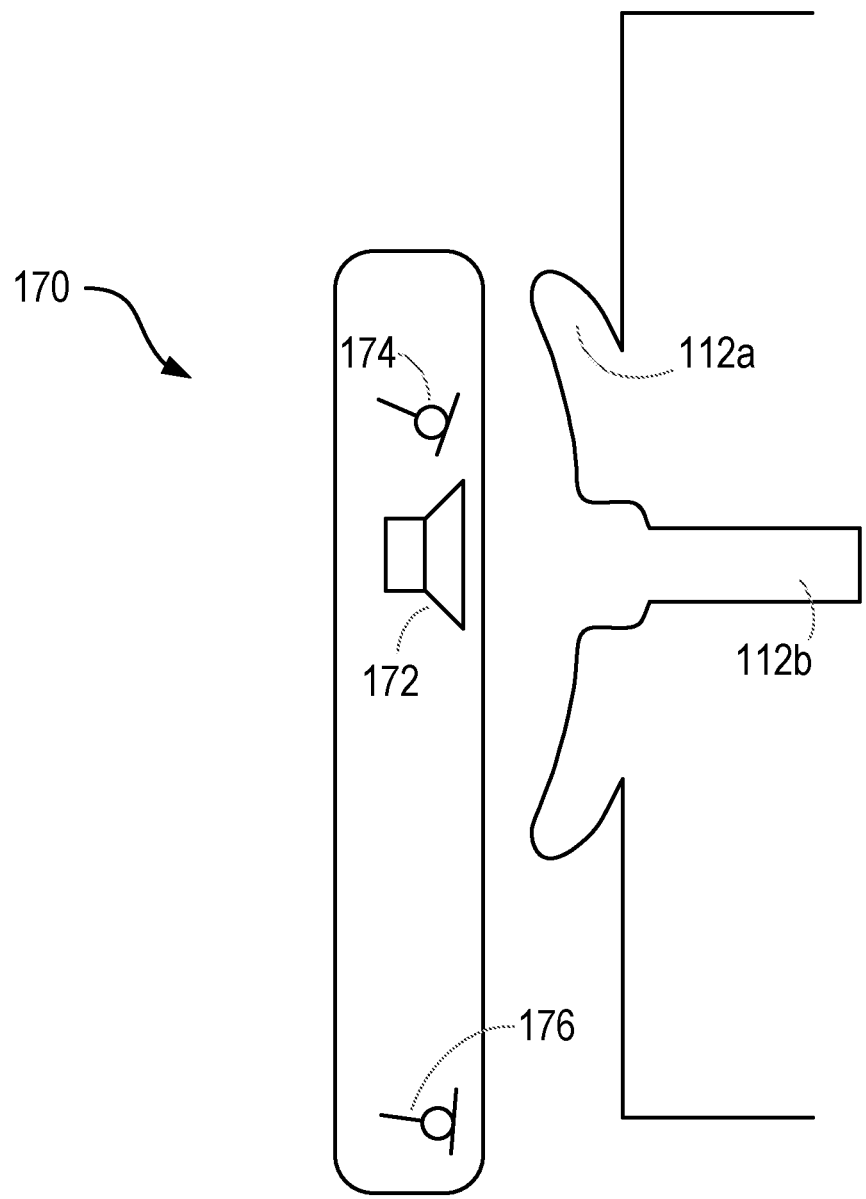
FIG. 1b shows a personal audio device according to another configuration.

FIG. 1a shows the application of an electronic device arrangement 100 to a user's ear, with the arrangement 100 comprising a personal audio device 150 (in the illustrated embodiment, an in-ear headphone or earphone, insert headphone, or ear bud) and a host device 160 (in the illustrated embodiment, a smartphone). In such an embodiment, the functionality discussed below may be provided solely in the personal audio device 150, solely in the host device 160, or split between both devices (i.e. with each device performing different aspects). FIG. 1b shows the application of a personal audio device 170 (in the illustrated embodiment, a smartphone) to a user's ear. In this example, therefore, there is no separate host device and the functionality discussed below is carried out in the personal audio device itself.

FIG. 1a shows a schematic diagram of a user's ear, comprising the (external) pinna or auricle 112a, and the (internal) ear canal 112b. An electronic device arrangement 100 comprises a personal audio device 150 and a host device 160.

As noted above, in the illustrated embodiment the personal audio device 150 comprises an in-ear headphone (or earphone), insert headphone, or ear bud. This headphone is configured to be partially or totally inserted within the ear canal 112b, and may provide a relatively tight seal between the ear canal 112b and the external environment (i.e., it may be acoustically closed or sealed). Alternative personal audio devices include circum-aural headphones (e.g., those headphones comprising a shell which substantially surrounds and encloses the auricle), supra-aural headphones (e.g., those headphones which do not surround or enclose the user's ear, but rather sit on the auricle 112a), intra-concha headphones or earphones (e.g., those headphones which sit inside the user's concha cavity), and smartphones or mobile phones etc. (see FIG. 1b).

The personal audio device 150 comprises one or more loudspeakers 152 and one or more microphones 154. The one or more loudspeakers 152 are positioned on an internal surface of the headphone, and arranged to generate acoustic signals (e.g., audible or inaudible signals, such as ultrasonic waves) towards the user's ear and particularly the ear canal 112b. The one or more microphones 154 (hereinafter, "ear microphones") are also positioned on the internal surface of the headphone, and arranged to detect acoustic signals within the internal volume defined by the headphone (in the illustrated embodiment, the ear canal 112b).

The headphone may be able to perform active noise cancellation, to reduce the amount of noise experienced by the user of the headphone. Active noise cancellation operates by detecting a noise (i.e. with a microphone), and generating a signal (i.e. with a loudspeaker) that has the same amplitude as the noise signal but is opposite in phase. The generated signal thus interferes destructively with the noise and so lessens the noise experienced by the user. Active noise cancellation may operate on the basis of feedback signals, feedforward signals, or a combination of both. Feedforward active noise cancellation utilizes one or more microphones on an external surface of the headphone, operative to detect the environmental noise before it reaches the user's ear. The detected noise is processed quickly, and the cancellation signal generated so as to match the incoming noise as it arrives at the user's ear. Feedback active noise cancellation utilizes one or more error microphones positioned on the internal surface of the headphone, operative to detect the combination of the noise and the audio playback signal generated by the one or more loudspeakers. This combination is used in a feedback loop, together with knowledge of the audio playback signal, to adjust the cancelling signal generated by the loudspeaker and so reduce the noise. The ear microphone 154 shown in FIG. 1a may therefore form part of an active noise cancellation system, for example, as an error microphone.

The personal audio device 150 may comprise a further microphone 156 positioned such that, in use, the microphone 156 lies close to the user's mouth and therefore primarily detects the user's voice. The microphone 156 may be termed the voice microphone herein. In the illustrated embodiment, the voice microphone 156 is provided within the wired connection to the host device 160. In other embodiments, the voice microphone 156 may be provided on the end of an arm as part of a headset, for example.

The personal audio device 150 and the host device 160 may be operatively coupled together, such that signals and/or data can be passed between them. For example, signals detected by the microphones 154, 156 may be passed from the personal audio device 150 to the host device 160; audio signals to be played back to the user may be passed from the host device 160 to the personal audio device. In some embodiments, biometric authentication results may be passed between the personal audio device 150 and the host device 160.

In the illustrated embodiment, the personal audio device 150 is coupled to the host device 160 via a wired connection. Those skilled in the art will appreciate of course that any operative connection between the two devices may be provided, such as a wireless connection (e.g., Bluetooth®).

FIG. 1b shows an alternative personal audio device 170, which is a mobile or cellular phone or handset. The handset 170 comprises one or more loudspeakers 172 for audio playback to the user, one or more ear microphones 174 which are similarly positioned to detect acoustic signals in the vicinity of the user's ear, and one or more voice microphones 176 to detect the user's voice.

In use, the handset 170 is held close to the user's ear so as to provide audio playback (e.g. during a call). While a tight acoustic seal is not achieved between the handset 170 and the user's ear, the handset 170 is typically held close enough that an acoustic stimulus applied to the ear via the one or more loudspeakers 172 generates a response from the ear which can be detected by the one or more ear microphones 174. As with the other devices, the loudspeaker(s) 172 and ear microphone(s) 174 may form part of an active noise cancellation system.

Figure 2:
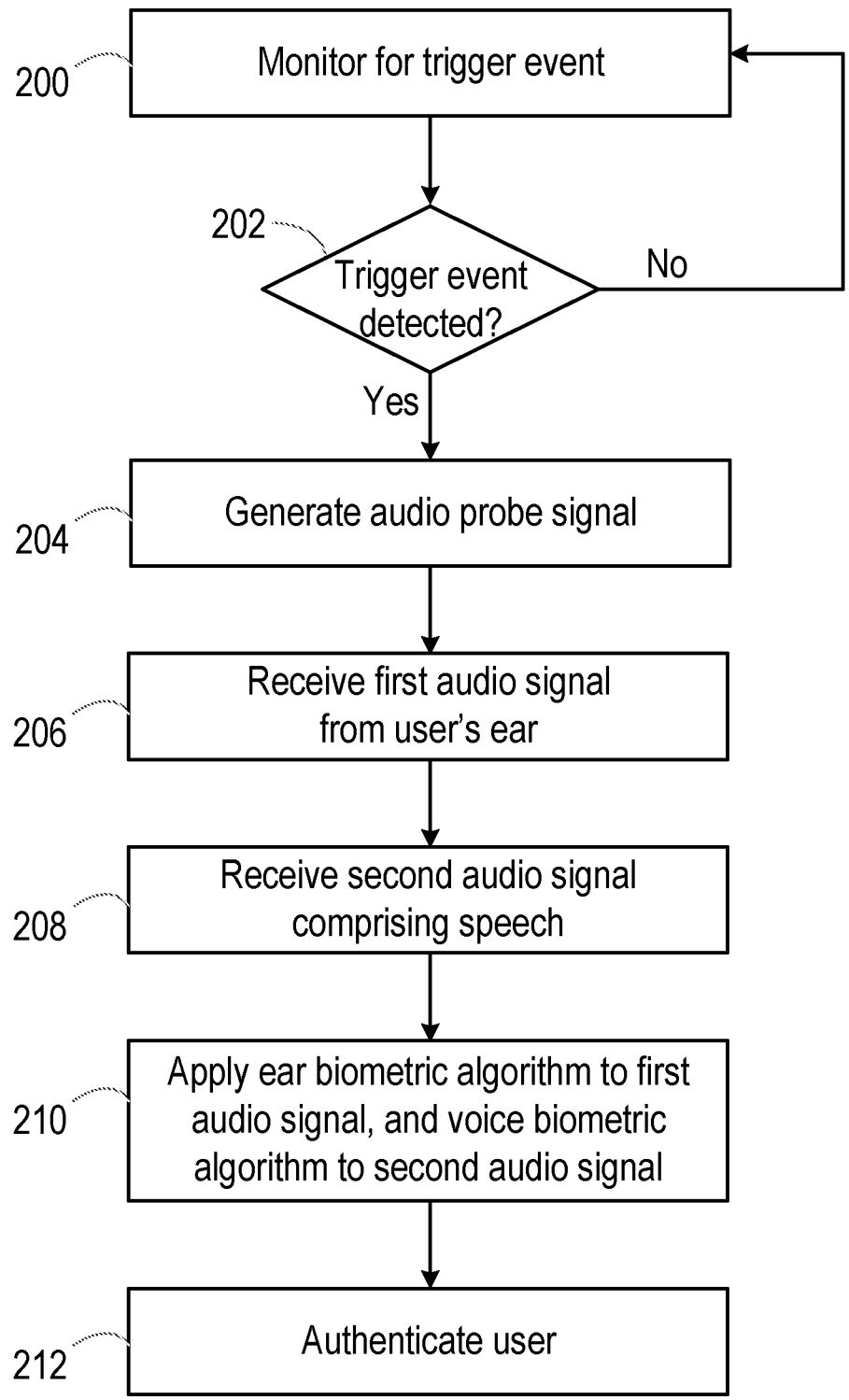
FIG. 2 is a flowchart of a method according to embodiments of the disclosure.

FIG. 2 is a flowchart of a method for authenticating a user as an authorised user of an electronic device. The method may utilize any of the personal audio devices discussed above with respect to FIGS. 1a and 1b, for example, and may be performed by an authentication device which is arranged exclusively within the personal audio device, exclusively within a host device coupled to that personal audio device, or which is distributed between the host device and the personal audio device.

In step 200, the authentication device monitors for an event which triggers the authentication process (hereinafter, "trigger event"). Various events are contemplated as trigger events according to embodiments of the disclosure.

In one embodiment, the trigger event is indicative of a user interaction with the authentication device. The trigger event may alternatively or additionally be indicative of a user's desire to interact with the personal audio device using speech. For example, the trigger event may be associated with activation of a virtual assistant, e.g., Siri, Cortana, Alexa (all®), etc.

The trigger event may comprise actuation of a physical or virtual button on the personal audio device. Personal audio devices often have such buttons in order to send control signals to the personal audio device and/or a host device. Different control signals may be generated based on the type of button actuation (e.g., a short or long press) or on a sequence of multiple button actuations (e.g., a chain of two or three button presses in sequence). The button may physically move in response to the user interaction (e.g., a physical button), or comprise a capacitive or ultrasonic sensor (e.g., a virtual button). In another example, a personal audio device may detect finger taps or other user interactions with the device via a microphone (such as the ear microphones 154, 174 and/or the voice microphones 156, 176). Pulses of audio detected by the microphone may be determined as being indicative of a tap of the user's fingers on the microphone. In this way, the microphone itself functions as a button. Trigger events in which a button is actuated (or its functional equivalent) consume small amounts of power.

In another example, the user interaction may be a spoken interaction. For example, the user may speak a predetermined word or phrase ("trigger phrase"), such as "Hey Siri", "OK Google", etc., which is detected by a trigger phrase detect module in the authentication device.

In step 202, it is determined whether a trigger event has been detected. If no trigger event has been detected, the method returns to step 200 and the authentication device continues to monitor for a trigger event. If a trigger event is detected, the authentication process is initiated and the method proceeds to step 204.

In step 204, the authentication device generates an audio probe signal to be played through an audio transducer of the personal audio device in the vicinity of the user's ear. For example, the audio probe signal may be played back through the loudspeakers 152, 172.

The audio probe signal may be audible or inaudible. In embodiments where the audio probe signal is inaudible, the signal may be ultrasonic (e.g., greater than 20 kHz or in the range 20 kHz to 50 kHz). In embodiments where the audio probe signal is audible, and where the trigger event is associated with a user's desire to interact with the authentication device via speech, the audio probe signal may comprise a prompt to the user to speak. The prompt may be explicit (e.g., speech from a virtual assistant) or implicit (e.g., a notification tone associated with speech input).

The audio probe signal may comprise any suitable signal which causes an acoustic response of the user's ear. For example, the audio probe signal may comprise a chirp of signals at one or more frequencies, white noise, a sound tone, music, speech, etc. In one embodiment, the audio probe signal may be selected or modulated to contain power at frequencies which stimulate frequencies in the acoustic response of the user's ear which are discriminative between different users. Frequencies which may be discriminative between different users include frequency bands between approximately 1 kHz and approximately 3 kHz; between approximately 5 kHz and approximately 7 kHz; and between approximately 10 kHz and approximately 12 kHz. For example, the speech output of a virtual assistant may be modified to contain power at frequencies which stimulate an acoustic response at those discriminative frequencies. Particular music samples may be chosen, or user-selected music adapted, to contain power at the appropriate frequencies.

In step 206, the authentication device receives a first audio signal comprising a response of the user's ear to play back of the audio probe signal. As noted above, the response may comprise the audio probe signal as modified by a transfer function associated with the user's ear. Alternatively or additionally, the response may comprise an otoacoustic emission from the user's ear. The first audio signal may be generated by a microphone in the vicinity of the user's ear, such as the ear microphones 154, 174.

In step 208, the authentication device further receives a second audio signal comprising speech of the user. The speech may comprise one or more commands or command phrases, e.g., instructions to be carried out by the personal audio device and/or the host device. The second audio signal may be generated by a voice microphone, such as the microphones 156, 176.

In embodiments where the audio probe signal comprises a prompt to the user to speak, the second audio signal may be received in response to that prompt.

In order to conserve power, the authentication device may monitor for the speech only in a limited time window. The time window may begin upon the audio probe signal ending, for example, and continue for a predetermined period of time. Alternatively, the time window may overlap with transmission of the audio probe signal. For example, if the probe signal is inaudible, the user will not be aware of it and consequently may provide speech (e.g., command speech) before or during the audio probe signal. Even if the probe signal is audible, a user may not wait for the audio probe signal before speaking. Consequently, the time window may be defined so as to overlap with transmission of the audio probe signal (e.g., starting before or during transmission of the audio probe signal) to increase the likelihood that all of the speech is acquired.

Alternatively or additionally, the time window may be defined based on speech detected in the first audio signal. In this regard, it is noted that speech detected in the first audio signal is highly likely to correspond to speech from the user rather than another person, owing to the location of the ear microphones close to, or inside the user's ear. That is, speech from the user detected by the ear microphone may have been conducted primarily through the user's skull and/or jaw bone and have a relatively high amplitude, while speech from others is likely to be attenuated (e.g., owing to a relatively tight acoustic coupling around the ear canal 112*b*).

The time window may therefore be defined based on those times at which the first audio signal is substantially correlated with the second audio signal. Alternatively or additionally, the time window may be defined based on those times at which speech input is detected in the first audio signal.

In step 210, the authentication device performs an ear biometric algorithm on the first audio signal, and a voice biometric algorithm on the second audio signal, to authenticate the user as an authorised user.

Each biometric algorithm may comprise the extraction of one or more features from the audio signal, and the comparison of those extracted features to corresponding features in a stored template for an authorised user. For example, a user will typically undergo a process known as enrolment, in which biometric data is obtained in a secure environment (e.g., once the user has already been authenticated via an alternative mechanism, or is deemed authenticated), and features are extracted from that biometric data and stored in a template for that user. The user may be required to provide multiple biometric inputs to increase the reliability of the features extracted for the purposes of the template. For example, several samples of ear biometric data may be acquired, or the user may be required to provide multiple spoken inputs as voice biometric data.

In step 210, the relevant features are extracted from the first and second audio signals, and compared to the features in those stored templates. Thus, one or more features are extracted from the first audio signal, and compared to corresponding features of the ear biometric template for the authorised user. Similarly, one or more features are extracted from the second audio signal, and compared to corresponding features of the voice biometric template for the authorised user.

One or more biometric scores may be generated, indicative of the likelihood that the user (i.e., the user providing the biometric input) is the authorised user. For example, the score may be based on the mathematical distance (e.g., the cosine vector similarity or any other suitable comparison algorithm) between the obtained features and the stored features. The one or more biometric scores may then be compared to one or more threshold values in order to decide whether the user should be authenticated as the authorised user or not.

The outputs of the voice and ear biometric algorithms may be combined or fused in order to authenticate the user. Various methods of biometric fusion are known in the art, and the present disclosure is not limited in that respect. For example, separate biometric scores may be generated for the ear biometric algorithm and the voice biometric algorithm, and these biometric scores compared to separate threshold values in order to generate separate biometric results. These results may then be fused to generate an overall authentication decision or result (result-level fusion). For example, the user may be authenticated as the authorised user only if both ear and voice biometric results are positive. Alternatively, the separate biometric scores may be combined to generate an overall score, with this overall score then being compared to a threshold value (score-level fusion).

In embodiments where the trigger event comprises a trigger phrase uttered by the user (e.g., a predetermined phrase or word, such as "Hey Siri", "OK Google", etc.), a voice biometric algorithm may additionally be performed on features extracted from that trigger phrase, and the overall authentication decision or result based additionally on that voice biometric algorithm.

For example, the voice biometric algorithm may be performed on the predetermined phrase to obtain a first voice biometric score, and also on the command speech (e.g. from the second audio signal) to obtain a second voice biometric score. The first and second voice biometric scores may be fused with the ear biometric score to obtain an overall biometric score which can be compared to one or more thresholds to obtain an overall biometric result. Alternatively, as noted above, separate biometric results may be obtained for each biometric process (e.g., based on the first and second voice biometric scores and the ear biometric score) and the results fused to obtain an overall biometric result.

In step 212, the user is authenticated as the authorised user, or denied authentication, based on the ear and voice biometric algorithms performed in step 210.

Figure 3:
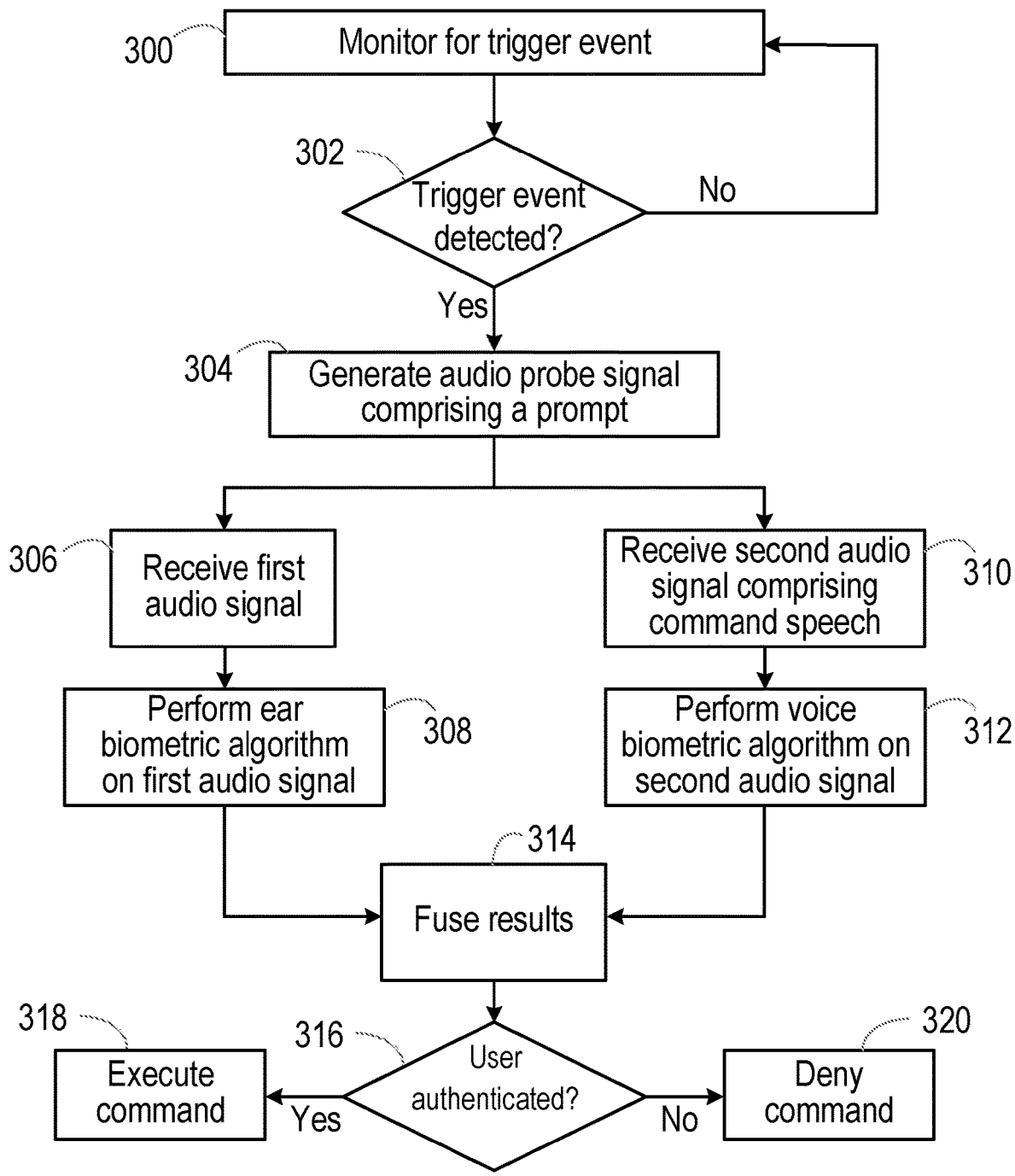
FIG. 3 is a flowchart of a method according to further embodiments of the disclosure.

FIG. 3 is a flowchart of a method according to further embodiments of the disclosure. Again, the method may be performed by an authentication device which is arranged exclusively within a personal audio device, exclusively within a host device coupled to that personal audio device, or which is distributed between the host device and the personal audio device.

In step 300, the authentication device monitors for an event which triggers the authentication process (hereinafter, "trigger event"). Various events are contemplated as trigger events according to embodiments of the disclosure.

In one embodiment, the trigger event is indicative of a physical interaction with the authentication device. The trigger event may alternatively or additionally be indicative of a user's desire to interact with the personal audio device using speech. For example, the trigger event may be associated with activation of a virtual assistant, e.g., Siri, Cortana, Alexa (all®), etc.

The trigger event may comprise actuation of a physical or virtual button on the personal audio device. Personal audio devices often have such buttons in order to send control signals to the personal audio device and/or a host device. Different control signals may be generated based on the type of button actuation (e.g., a short or long press) or on a sequence of multiple button actuations (e.g., a chain of two or three button presses in sequence). The button may physically move in response to the user interaction (e.g., a physical button), or comprise a capacitive or ultrasonic sensor (e.g., a virtual button). In another example, a personal audio device may detect finger taps or other user interactions with the device via a microphone (such as the ear microphones 154, 174 and/or the voice microphones 156, 176). Pulses of audio detected by the microphone may be determined as being indicative of a tap of the user's fingers on the microphone. In this way, the microphone itself functions as a button. Trigger events in which a button is actuated (or its functional equivalent) consume small amounts of power.

In step 302, it is determined whether a trigger event has been detected. If no trigger event has been detected, the method returns to step 300 and the authentication device continues to monitor for a trigger event. If a trigger event is detected, the authentication process is initiated and the method proceeds to step 304.

In step 304, the authentication device generates an audio probe signal to be played through an audio transducer of the personal audio device in the vicinity of the user's ear. For example, the audio probe signal may be played back through the loudspeakers 152, 172.

The audio probe signal is audible, and may comprise a prompt to the user to speak. The prompt may be explicit (e.g., speech from a virtual assistant) or implicit (e.g., a notification tone associated with speech input).

The audio probe signal may comprise any suitable signal which causes an acoustic response of the user's ear. For example, the audio probe signal may comprise a chirp of signals at one or more frequencies, white noise, a sound tone, music, speech, etc. In one embodiment, the audio probe signal may be selected or modulated to contain power at frequencies which stimulate frequencies in the acoustic response of the user's ear which are discriminative between different users. Frequencies which may be discriminative between different users include frequency bands between approximately 1 kHz and approximately 3 kHz; between approximately 5 kHz and approximately 7 kHz; and between approximately 10 kHz and approximately 12 kHz. For example, the speech output of a virtual assistant may be modified to contain power at frequencies which stimulate an acoustic response at those discriminative frequencies. Particular music samples may be chosen, or user-selected music adapted, to contain power at the appropriate frequencies.

In step 306, the authentication device receives a first audio signal comprising a response of the user's ear to play back of the audio probe signal. As noted above, the response may comprise the audio probe signal as modified by a transfer function associated with the user's ear. Alternatively or additionally, the response may comprise an otoacoustic emission from the user's ear. The first audio signal may be generated by a microphone in the vicinity of the user's ear, such as the ear microphones 154, 174.

In step 308, the authentication device performs an ear biometric algorithm on the first audio signal. Thus, one or more features are extracted from the first audio signal, and compared to corresponding features of an ear biometric template for an authorised user (or the templates for multiple authorised users if they exist). An ear biometric score is generated, indicative of the likelihood that the user (i.e., the user providing the ear biometric input) is an authorised user, based on the ear biometric algorithm. For example, the score may be based on the mathematical distance (e.g., the cosine vector similarity or any other suitable comparison algorithm) between the obtained features and the stored features.

In step 310, and in parallel to steps 306 and 308 in the illustrated embodiment, the authentication device further receives a second audio signal comprising speech of the user in response to the prompt contained in the audio probe signal. The speech may comprise one or more commands or command phrases, e.g., instructions to be carried out by the personal audio device and/or the host device. The second audio signal may be generated by a voice microphone, such as the microphones 156, 176.

In order to conserve power, the authentication device may monitor for the speech only in a limited time window. The time window may begin upon the audio probe signal ending, for example, and continue for a predetermined period of time.

Alternatively or additionally, the time window may be defined based on speech detected in the first audio signal. In this regard, it is noted that speech detected in the first audio signal is highly likely to correspond to speech from the user rather than another person, owing to the location of the ear microphones close to, or inside the user's ear. That is, speech from the user detected by the ear microphone may have been conducted primarily through the user's skull and/or jaw bone and have a relatively high amplitude, while speech from others is likely to be attenuated. The time window may therefore be defined based on those times at which the first audio signal is substantially correlated with the second audio signal. Alternatively or additionally, the time window may be defined based on those times at which speech input is detected in the first audio signal.

In step 312, the authentication device performs a voice biometric algorithm on the second audio signal. Thus, one or more features are extracted from the second audio signal, and compared to corresponding features of the voice biometric template for the authorised user (or multiple voice biometric templates for multiple authorised users if they exist).

In step 314, the outputs of the voice and ear biometric algorithms are combined or fused in order to authenticate the user. In the illustrated embodiment, result-level fusion is utilized to fuse the results of the ear and voice biometric algorithms, i.e., the ear and voice biometric scores are compared to separate thresholds to generate corresponding results, and the results are combined. Alternatively, the separate biometric scores may be combined to generate an overall score, with this overall score then being compared to a threshold value (score-level fusion).

In step 316, it is determined whether the user was authenticated as a result of the combined voice and ear biometric algorithms. If the authentication is positive, the method proceeds to step 318, in which the command spoken by the user in the second audio signal is executed. If the authentication is negative, the method proceeds to step 320 in which the command spoken by the user is denied or not executed. In this regard, speech recognition may be performed on the second audio signal (e.g., the gated parts of the second audio signal) in order to determine the semantic meaning of the command speech. Speech recognition may be performed locally (e.g., in the host device or the personal audio device if they have sufficient processing capability), or remotely in a speech recognition service. In the latter case, the second audio signal may be transmitted to the speech recognition service to be processed.

Figure 4:
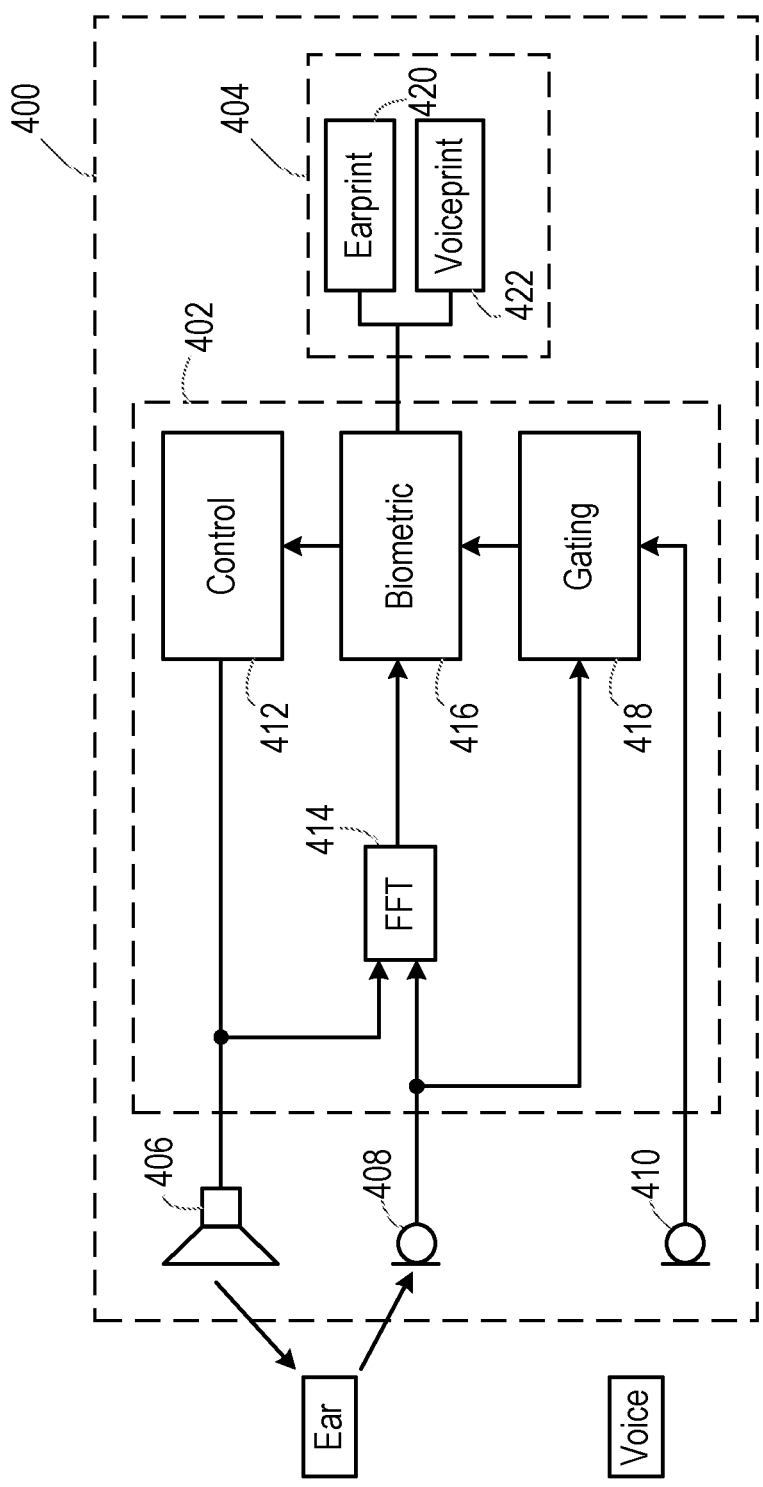
FIG. 4 is a schematic diagram of a biometric authentication system according to embodiments of the disclosure.

FIG. 4 shows a schematic diagram of an authentication system 400 according to embodiments of the disclosure. The authentication system 400 comprises an authentication device 402 or processing circuitry (which may be implemented on one or more integrated circuits), a memory 404, and one or more input and output devices described below. As noted above, the authentication device 402 may be provided exclusively within a personal audio device, exclusively within a host device coupled to the personal audio device, or distributed between the personal audio device and the host device. The memory 404 may similarly be provided within the personal audio device, within the host device, or distributed between the personal audio device and the host device.

The system 400 comprises a loudspeaker 406, which may be a microspeaker. The loudspeaker 406 may be arranged within the personal audio device, such that it is located next to a user's ear during use. For example, the loudspeaker 406 may correspond to either of the loudspeakers 152, 172 described above with respect to FIGS. 1*a* and 1*b*.

The system 400 further comprises an ear microphone 408. The ear microphone 408 may be arranged within the personal audio device, such that it is located next to a user's ear during use. For example, the ear microphone 408 may correspond to either of the microphones 154, 174 described above with respect to FIGS. 1*a* and 1*b*.

The system 400 further comprises a voice microphone 410. The voice microphone 410 may be arranged within the personal audio device, such that it is located next to a user's mouth during use. For example, the voice microphone 410 may correspond to either of the microphones 156, 176 described above with respect to FIGS. 1*a* and 1*b*.

The device 402 comprises a control module 412 which is operative to receive or detect a trigger event, e.g., as described above with respect to steps 200 and/or 300. Responsive to detection of the trigger event, the control module 412 generates an audio probe signal to be played back to the user via the loudspeaker 406.

The audio probe signal may be audible or inaudible. In embodiments where the audio probe signal is inaudible, the signal may be ultrasonic (e.g., greater than 20 kHz or in the range 20 kHz to 50 kHz). In embodiments where the audio probe signal is audible, and where the trigger event is associated with a user's desire to interact with the authentication device via speech, the audio probe signal may comprise a prompt to the user to speak. The prompt may be explicit (e.g., speech from a virtual assistant) or implicit (e.g., a notification tone associated with speech input).

The audio probe signal may comprise any suitable signal which causes an acoustic response of the user's ear. For example, the audio probe signal may comprise a chirp of signals at one or more frequencies, white noise, a sound tone, music, speech, etc. In one embodiment, the audio probe signal may be selected or modulated to contain power at frequencies which stimulate frequencies in the acoustic response of the user's ear which are discriminative between different users. Frequencies which may be discriminative between different users include frequency bands between approximately 1 kHz and approximately 3 kHz; between approximately 5 kHz and approximately 7 kHz; and between approximately 10 kHz and approximately 12 kHz. For example, the speech output of a virtual assistant may be modified to contain power at frequencies which stimulate an acoustic response at those discriminative frequencies. Particular music samples may be chosen, or user-selected music adapted, to contain power at the appropriate frequencies.

The ear microphone 408 detects the acoustic response of the user's ear, and generates a first audio signal. The first audio signal is detected by the microphone 408 in the time domain. However, the features extracted for the purposes of the biometric process may be in the frequency domain (in that it is the frequency response of the user's ear which is characteristic). The device 402 therefore comprises a Fourier transform module 414, which converts the first audio signal to the frequency domain. For example, the Fourier transform module 414 may implement a fast Fourier transform (FFT). In some examples the biometric process may not be in the frequency domain, so the Fourier transform module may be omitted.

The output of the Fourier transform module 414 is provided to a biometric authentication module 416, which is configured to perform an ear biometric algorithm on the signal, e.g., as described above with respect to steps 210 and 308. Thus the biometric authentication module 416 extracts one or more features from the first audio signal and compares those features to a stored ear template 420 for an authorised user (e.g., an "ear print"), for example as stored in the memory 404.

In some embodiments the biometric authentication module 416 may be designed to extract features with foreknowledge of the nature of the audio probe signal, for example knowing the spectrum of the audio probe signal, so that the response or transfer function may be appropriately normalised. In other embodiments the Fourier transform module 414 may comprise a second input to monitor the audio probe signal (e.g. playback music) and hence provide the biometric authentication module 416 with information about the audio probe signal or its spectrum so that the biometric authentication module may calculate the transfer function from the audio probe signal to the received acoustic waveform, from which it may derive the desired feature parameters.

The voice microphone 410 generates a second audio signal comprising speech of the user (e.g., in response to a prompt in the audio probe signal). The second audio signal is also provided to the biometric authentication module 416, which is configured to perform a voice biometric algorithm on the signal, e.g., as described above with respect to steps 210 and 312. Thus the biometric authentication module 416 extracts one or more features from the second audio signal and compares those features to a stored voice template 422 for an authorised user (e.g., a "voice print"), for example as stored in the memory 404. As noted above, the biometric authentication module 416 may additionally perform a voice biometric algorithm on a trigger phrase or word uttered by the user (e.g., and detected as a trigger event to commence authentication).

As noted above, in some embodiments the second audio signal is gated, and thus in the illustrated embodiment the authentication device 402 further comprises a gating module 418 which is operative to receive the second audio signal from the voice microphone 410, and to provide a gated signal to the biometric authentication module 416. The gating may be such that the biometric algorithm is performed only on the second audio signal in a limited time window. The time window may begin upon the audio probe signal ending, for example, and continue for a predetermined period of time. In such embodiments, the control module 412 may provide a gating signal to the gating module 418 indicating when the audio probe signal has ended.

Alternatively or additionally, the time window may be defined based on speech detected in the first audio signal. Thus, in the illustrated embodiment, the first audio signal is also provided to the gating module 418. The time window may therefore be defined based on those times at which the first audio signal is substantially correlated with the second audio signal. Alternatively or additionally, the time window may be defined based on those times at which speech input is detected in the first audio signal, e.g., using a voice activity detector (not illustrated).

The biometric authentication module 416 is operative to authenticate the user as an authorised user based on the ear biometric algorithm and the voice biometric algorithm. An overall biometric authentication result may be output from the biometric authentication module 416 to, for example, the control module 412 for further processing (e.g., performing or denying a requested task).

Thus embodiments of the present disclosure provide a convenient mechanism for authenticating a user as an authorised user based on ear and voice biometrics.

Embodiments described above have focussed on an implementation in which ear biometrics are performed on signals detected in a single ear. It will be appreciated by those skilled in the art that the embodiments may straightforwardly be adapted to take into consideration biometric data obtained from both ears of a user. Thus, where the description above discloses acquiring data from an ear, data may similarly be acquired from two ears. Biometric algorithms may similarly be performed on data from both ears, and this may be combined as described above, i.e. separate biometric authentication scores combined to form a combined score on which an overall decision is determined, or separate biometric authentication decisions which are then combined to determine an overall decision.

Embodiments may be implemented in an electronic, portable and/or battery powered host device such as a smartphone, an audio player, a mobile or cellular phone, or a handset. Embodiments may be implemented on one or more integrated circuits provided within such a host device. Embodiments may be implemented in a personal audio device configurable to provide audio playback to a single person, such as a smartphone, a mobile or cellular phone, headset, headphones, earphones. Again, embodiments may be implemented on one or more integrated circuits provided within such a personal audio device. In yet further alternatives, embodiments may be implemented in a combination of a host device and a personal audio device. For example, embodiments may be implemented in one or more integrated circuits provided within the personal audio device, and one or more integrated circuits provided within the host device.

It should be understood—especially by those having ordinary skill in the art with the benefit of this disclosure— that the various operations described herein, particularly in connection with the figures, may be implemented by other circuitry or other hardware components. The order in which each operation of a given method is performed may be changed, and various elements of the systems illustrated herein may be added, reordered, combined, omitted, modified, etc. It is intended that this disclosure embrace all such modifications and changes and, accordingly, the above description should be regarded in an illustrative rather than a restrictive sense.

Similarly, although this disclosure makes reference to specific embodiments, certain modifications and changes can be made to those embodiments without departing from the scope and coverage of this disclosure. Moreover, any benefits, advantages, or solutions to problems that are described herein with regard to specific embodiments are not intended to be construed as a critical, required, or essential feature or element.

Further embodiments likewise, with the benefit of this disclosure, will be apparent to those having ordinary skill in the art, and such embodiments should be deemed as being encompassed herein.

The invention claimed is:

1. A method for authenticating a user of an electronic device, the method comprising:
    responsive to detection of a trigger event indicative of a user interaction with the electronic device, generating an audio probe signal to play through an audio transducer of the electronic device, the audio probe signal comprising an audible prompt to the user to speak;
    receiving a first audio signal comprising a response of the user's ear to the audio probe signal;
    receiving a second audio signal comprising bone-conducted speech of the user in response to the audible prompt to speak; and
    applying an ear biometric algorithm to the first audio signal and a voice biometric algorithm to the second audio signal to authenticate the user as an authorised user.

2. The method according to claim 1, wherein the audio probe signal comprises a prompt to the user to speak, and wherein the second audio signal is received in response to the prompt.

3. The method according to claim 1, wherein the ear biometric algorithm comprises generation of an ear biometric score based on the comparison, and voice biometric algorithm comprises generation of a voice biometric score based on the comparison.

4. The method according to claim 3, wherein the ear biometric score and the voice biometric score are fused to generate a combined biometric score, and wherein the combined biometric score is compared to one or more threshold values to generate a combined biometric result.

5. The method according to claim 3, wherein the ear biometric score is compared to a first threshold value to generate an ear biometric result, wherein the voice biometric score is compared to a second threshold value to generate a voice biometric result, and wherein the ear biometric result is combined with voice biometric result to generate a combined biometric result.

6. An authentication device for authenticating a user of an electronic device, the authentication device comprising:
    an audio signal generation module for generating, responsive to detection of a trigger event indicative of a user interaction with the electronic device, an audio probe signal to play through an audio transducer of the electronic device, the audio probe signal comprising an audible prompt to the user to speak;
    one or more inputs for receiving a first audio signal comprising a response of the user's ear to the audio probe signal, and a second audio signal comprising bone-conducted speech of the user in response to the audible prompt to speak; and
    a biometric authentication module for utilizing an ear biometric algorithm on the first audio signal and a voice biometric algorithm on the second audio signal to authenticate the user as an authorised user.

7. The authentication device according to claim 6, wherein the audio probe signal comprises a prompt to the user to speak, and wherein the second audio signal is received in response to the prompt.

8. The authentication device according to claim 6, wherein the ear biometric algorithm comprises generation of an ear biometric score based on the comparison, and the voice biometric algorithm comprises generation of a voice biometric score based on the comparison.

9. The authentication device according to claim 8, wherein the ear biometric score and the voice biometric score are fused to generate a combined biometric score, and wherein the combined biometric score is compared to one or more threshold values to generate a combined biometric result.

10. The authentication device according to claim 8, wherein the ear biometric score is compared to a first threshold value to generate an ear biometric result, wherein the voice biometric score is compared to a second threshold value to generate a voice biometric result, and wherein the ear biometric result is combined with voice biometric result to generate a combined biometric result.

11. The authentication device according to claim 8, wherein the ear biometric score is generated based on a comparison between one or more features extracted from the first audio signal and corresponding features of an ear biometric template for the authorised user.

12. The authentication device according to claim 8, wherein the voice biometric score is generated based on a comparison between one or more features extracted from the second audio signal and corresponding features of a voice biometric template for the authorised user.

13. The authentication device according to claim 6, further comprising a gating module configured to monitor the second audio signal for the speech of the user in a time window.

14. The authentication device according to claim 13, wherein the time window is defined in dependence on a gating signal corresponding to detection of bone-conducted speech in the first audio signal.

15. The authentication device according to claim 6, wherein the audio probe signal is modulated to stimulate the response of the user's ear at one or more frequencies which are discriminative between different users.

16. The authentication device according to claim 6, wherein the response of the user's ear comprises one or more of a frequency response of the user's ear canal and an oto-acoustic emission of the user's ear.

17. The authentication device according to claim 6, wherein the trigger event comprises a spoken predetermined keyword by the user.

18. The authentication device according to claim 6, wherein the trigger event comprises a physical interaction by the user with the electronic device.

19. The authentication device according to claim 6, wherein the speech of the user in response to the prompt comprises a command for execution by the electronic device.

20. An electronic device comprising the authentication device according to claim 6.

* * * * *